United States Patent [19]

Safai-Ghomi

[11] Patent Number: 5,849,302

[45] Date of Patent: Dec. 15, 1998

[54] MEDICAMENTS AND COSMETICS COMPRISING *ZIZYPHUS SPINA-CHRISTI* EXTRACTS

[76] Inventor: Mina Safai-Ghomi, Flat 6, 75 Belgrave Road, London SW1V 2BG, Great Britain

[21] Appl. No.: 889,211

[22] Filed: Jul. 7, 1997

[30]  Foreign Application Priority Data

Jul. 4, 1996 [GB] United Kingdom ............... 9614047

[51] Int. Cl.⁶ .................... A61K 33/78; A61K 7/48
[52] U.S. Cl. .............. 424/195.1; 424/701; 424/401
[58] Field of Search ................ 424/195.1, 701, 424/401

[56]  References Cited

U.S. PATENT DOCUMENTS 5,318,776  6/1994  Sigiyama et al. ............... 424/70

*Primary Examiner*—Jyothsna Venkai
*Attorney, Agent, or Firm*—Kubovcik & Kubovcik

[57]  ABSTRACT

Methods utilising extracts of the leaves of *Zizyphus spina-christi* are disclosed. These comprise cosmetic treatment and use in the manufacture of a medicament for treating psoriasis.

1 Claim, No Drawings

MEDICAMENTS AND COSMETICS COMPRISING *ZIZYPHUS SPINA-CHRISTI* EXTRACTS

This invention relates to medicaments and cosmetics comprising extracts of *Zizyphus spina-christi*. The invention has utility in cosmetic hair treatment by reversing greying.

Psoriasis causes much distress. Those afflicted suffer from discomfort and pain occasioned by the disease. The degree of discomfort is perhaps not fully appreciated by those not having the misfortune to suffer. Psoriasis is characterised by unsightly circumscribed red skin patches covered with white scale. Those affected suffer not only from as it were the medical effects of the complaint but also the physical effects. Sufferers can be very upset by their physical appearance in that damage is done to the self-image and also the sufferer feels he or she is being stared at by others. The stress occasioned by loss of self-image and real or imagined looks from passers-by leads to further spreading and so on.

Greying of hair so far as is known causes no damage to the body. The damage to the ego can be notoriously severe.

The invention seeks to alleviate the symptoms of these complaints in at least some cases. It must however be appreciated that psoriasis may not properly be considered to be a single disease. A more accurate analysis is that the complaint is a constellation of similar symptoms invoked by a variety of causes. Accordingly alleviation can not be expected in all cases. Nevertheless the invention has more than a placebo effect.

According to one aspect, the invention provides the use of an extract of dried leaves of *Zizyphus spina-christi* for use in the manufacture of a medicament for the treatment of psoriasis.

According to another aspect of the invention, there is provided a cosmetic method of improving the appearance of mammal afflicted by age-related grey air which is characterised by topical application of a composition comprising an extract of dried leaves of *Zizyphus spina-christi*.

The compositions derived from *Zizyphus spina-christi* are also effective in reducing skin inflammation, non specific erythema and itching. It may be desirable to apply them for example to sun-burn as cooling compositions. These compositions are also usable as skin cleansers for sensitive skin and are effective as excortication agents.

*Zizyphus spina-christi* is primarily found in the Middle East, including Iran and Iraq. The leaves are dried at low temperature and crushed to give a fine, pale green powder. Because zizyphus spp are not deciduous and leaves are always in a range of states of development the time of harvesting is not of crucial importance. A decoction of the powder prepared with hot water is pale coloured. When applied on the skin it has been found to reduce inflammation especially when caused by psoriasis. Application may be required daily or thrice weekly for some time before a significant improvement is noted.

The following composition is a non-limiting example:

| Ingredient | Amount/ml |
|---|---|
| Powdered dried leaves of *Zizyphus spina-christi* | 5 |
| Deionized water | 200 |

Warm water at 45° C. is poured over the powder and stirred. The liquor rapidly acquires some colour but is allowed to cool by standing. The liquor is decanted from the powder. Afflicted skin areas are bathed with liquor. After allowing contact for about five minutes the skin is patted dry.

The Zizyphus extract may be incorporated into a conventional shampoo or cream base for application. Ethanolic or other organic extraction of the leaves results, after removal of the solvent, in an oil which is efficacious. The oil or powder or decoction may be incorporated in any base for topical treatment. Examples include the shampoo base described with preservative or citrate. Application to the hair can reduce or reverse age-related greying of the hair.

Suitable strengths of decoction can be found by routine experiment. It is unlikely that any significant extra benefit can be obtained by using more than 20% Zizyphus (based on dry powder to final composition by volume). Similarly less than 0.5% is unlikely to have significantly greater than placebo effect. Preferred amounts are in the range of 1 to 15%, more preferably 2 to 10%, especially 3 to 6%.

The *Zizyphus spina-christi* leaves may be presented in other forms.

I claim:

1. A cosmetic method of improving the appearance of a mammal having age-related grey hair by topical application of a composition comprising an effective amount of extract of dried leaves of *Zizyphus spina-christi*.

* * * * *